United States Patent [19]

Holtkamp, Sr.

[11] Patent Number: Plant 6,439

[45] Date of Patent: Dec. 6, 1988

[54] AFRICAN VIOLET PLANT NAMED MISSISSIPPI

[76] Inventor: Reinhold Holtkamp, Sr., Werther Strasse 112, D4294 Isselburg, Fed. Rep. of Germany

[21] Appl. No.: 21,739

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Mississippi characterized by its large, single mainly white flowers with pink frilled edges and tinged with pink in the centers; strong, upright flower stems that curve toward the center to form a bouquet above the leaves, profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Mississippi.

The new cultivar was referred to during the breeding and selection process by the designation 110/1, and is a product of a planned breeding program. The new cultivar was originated from a cross made by me in the controlled breeding program in Isselburg, Federal Republic of Germany. The female, or seed parent was a cultivar designated D 198/5. The male, or pollen parent was a cultivar designated 4158.

Mississippi was discovered and selected by me in 1983 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Mississippi has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn. under greenhouse conditions which closely approximate those generally used in commercial practice.

The following traits have been repeatedly observed and are determined to be basic characteristics of Mississippi which in combination distinguish this African violet as a new and distinct cultivar:

(1) Strong, upright flower stems curving slightly toward the center.

(2) Large single variegated flower with white background and frilled light pink edges.

(3) First flash of flowers appears 9 weeks after potting and forms a tight bouquet above the leaves.

(4) Profuse flowering.

(5) Each plant carries 8–10 upright flower stems, each of which carries 5–7 and more flowers.

(6) Vigorous grower.

(7) Plant saleable 9 to 10 weeks after potting.

(8) Bright green, velvety, round leaves.

(9) Long lasting, non-dropping single flowers.

(10) Seed capsules push slightly through.

(11) Two stems come out of each axle.

(12) After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 2 p.m. in Nashville, Tenn.

Botanical classification: *Saintpaulia ionantha,* Ramat., cv. Mississippi.

Parentage:

*Male parent.*—4158.

*Female parent.*—D 198/5.

Propagation: The new cultivar holds its distinguishing characteristics through successive propagations by leaf cuttings.

Plant: From 8 cm to 10 cm tall when grown in pots, and approximately 23–25 cm in diameter when fully grown.

*Leaves.*—General form: round. Diameter: 60–70 mm. Texture: velvety. Aspect: hairy, shiny, slightly serrated. Veins: upperside: visible; underside: underside: well pronounced, light green shiny. Color (upper side): yellow green group 147A. Color (under side): yellow green group 148D. Petiole: strong, upright, light green, hairy.

*Flowers.*—Buds: ball-shaped, 7–8 mm before opening. Sepals: five (5). Color: green. Calyx: Shape: funnel shaped. Aspect: spear-shaped, hairy. Peduncle: strong upright, green sometimes with light purplish touch, hairy. Individual flowers: Size: 45–50 mm. Shape: single violet-shaped, frilled edges. Color (upper side): white with pink 49A-B on edges. Under cooler temperatures and more intensive lighting, the pink tends to intensify. Color (under side): white with 49C on edges. Borne: Each flower stem carries 5–7 and more flowers on strong upright wirelike peduncles that are free standing above the leaves, thereby forming a compact bouquet. Flowering habit: In flower 9 weeks after potting.

*Reproductive organs.*—Stamens: 2. Anthers: 2 composed of 4 anther cells, seed capsule pushes slightly through. Filaments: yellowish green, 4 mm long. Pollen Color: yellow group 7. Styles: 6 mm long, pinkish white, base of ovary light green.

*Roots.*—Normally developed, white when young, turning slightly brownish when older.

Disease resistance: Good.

General observations: Mississippi is a vigorous grower and early bloomer, with each stem carrying 5–7 large, single, variegated flowers with frilled edges. The flowers are mainly white with a touch of light pink in the center and a pink edge that varies between 1–5 mm in width. The intensity of the pink color can vary from one plant to another. The bright green, velvety, slightly serrated leaves give the plant a fresh look. The fully developed flower head forms a tight bouquet that is free-standing above the leaves. Approximately 9–10 weeks after potting the plant is saleable. The flowers are long lasting and non-dropping, and the seed capsule pushes slightly through.

I claim:

1. A new and distinct cultivar of African violet named Mississippi, as described and illustrated, and particularly characterized by its large, single mainly white flowers with pink frilled edges and tinged with pink in the centers; strong, upright flower stems that curve toward the center to form a bouquet above the leaves, profuse flowering, vigorous growth habit, flowering 9–10 weeks after potting, and its long-lasting and non-dropping flowers.

* * * * *

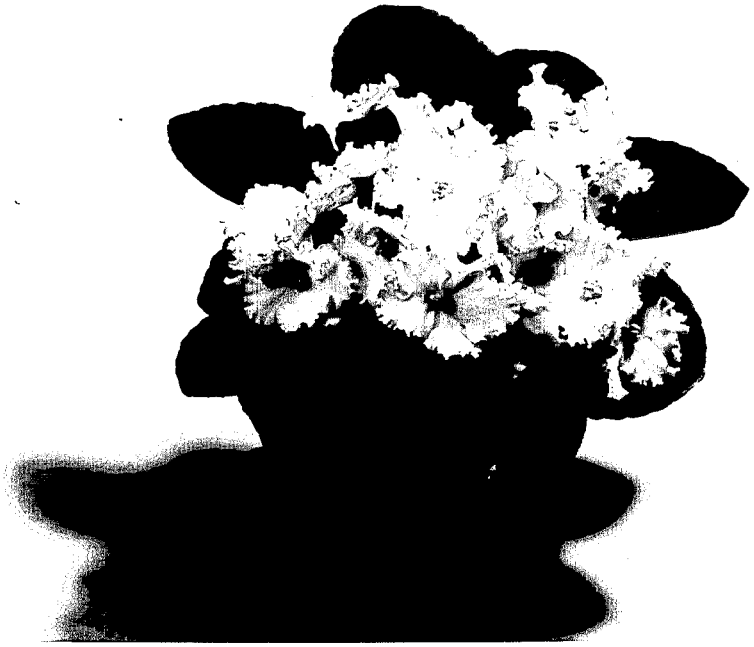
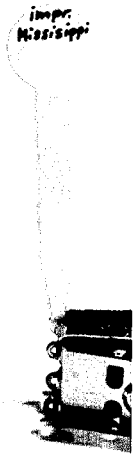
impr.
Mississippi